United States Patent [19]

Abu-El-Haj et al.

[11] 3,939,174

[45] Feb. 17, 1976

[54] CERTAIN 3-OXO-2-ARYL-5,6-DIHYDRO-4(H)-PYRROLO-(1,2-C)(1,2,3)TRIAZOLIUM COMPOUNDS

[75] Inventors: Marwan J. Abu-El-Haj, Groton; James W. McFarland, Lyme, both of Conn.

[73] Assignee: Pfizer Inc., New York, N.Y.

[22] Filed: Dec. 13, 1974

[21] Appl. No.: 532,495

Related U.S. Application Data

[60] Division of Ser. No. 395,713, Sept. 10, 1973, which is a continuation-in-part of Ser. No. 170,996, Aug. 11, 1971, abandoned.

[52] U.S. Cl................ 260/308 A; 71/90; 71/92; 260/296 H; 260/306.7 R
[51] Int. Cl.$^2$.............. C07D 249/06; C07D 471/04; C07D 513/04
[58] Field of Search................................ 260/308 A

[56] References Cited
UNITED STATES PATENTS
2,705,713   4/1955   Kendall et al.................. 260/308 A

OTHER PUBLICATIONS

Potts et al., J. Org. Chem., Vol. 35, pp. 3451–3456 (1970).

Abu–El–Haj et al., Chem. Abstracts, Vol. 78, Abstract No. 136300r (1973).

Begtrup et al., Chem. Abstracts, Vol. 76, Abstract No. 72454t (1972).

Primary Examiner—Alton D. Rollins
Attorney, Agent, or Firm—Connolly and Hutz

[57] ABSTRACT

A process for inhibiting plant growth comprising contacting a plant or its growth area with an effective amount of certain para-halophenyl substituted triazolines. A series of novel mesoionic para-halophenyl substituted triazolines. A novel process for preparing 3-phenyl-4-oxo-1,2,3-triazoline by contacting benzenediazoniumchloride and an α-amino carboxylic acid and cyclodehydrating the triazene produced using acetic anhydride and pyridine.

2 Claims, No Drawings

CERTAIN 3-OXO-2-ARYL-5,6-DIHYDRO-4(H)-PYRROLO-(1,2-C)(1,2,3)TRIAZOLIUM COMPOUNDS

CROSS REFERENCE TO RELATED APPLICATIONS

This application is a division of application Ser. No. 395,713 filed Sept. 10, 1973 which is a continuation in part of application Ser. No. 170,996 filed Aug. 11, 1971 now abandoned.

BACKGROUND OF THE INVENTION

The present invention relates to the field of control of plant growth. In particular it relates to methods and compounds for killing weeds and a novel process for preparing such compounds.

The term weed is used in the present disclosure in its broadest sense, that is, a plant which persists in growing where it is not wanted. This use of the term is broad enough to include plants such as poison ivy or other plants plainly harmful to man and also otherwise desirable plants such as honeysuckle or lawn grasses growing in such places as driveways.

SUMMARY OF THE INVENTION

The objects of this invention are threefold. One object is to provide a process for inhibiting plant growth which comprises contacting a plant or its growth area with an effective amount of:
4-oxo-1-substituted-3-(4-halophenyl)-1,2,3-triazole wherein such substituent is alkyl of from 2 to 5 carbon atoms or cycloalkyl of 5 to 6 carbon atoms;
3-oxo-2-(4-halophenyl)-4,5,6,7-tetrahydro-v-triazolo[1,5a]-pyridine;
3-oxo-2-(4-halophenyl)-5,6-dihydro-4(H)-pyrrolo-[1,2-c]-v-triazole;
or 3-oxo-2-(4-halophenyl)-4,6-dihydrothiazolo[3,4-c]-v-triazole.

The second object of this invention is to provide novel 4-halophenyl herbicides of the formulae:

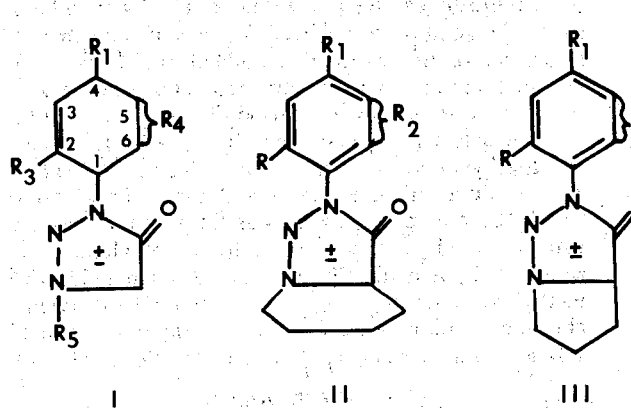

wherein: R is hydrogen, halogen, methyl or nitro; $R_1$ is halogen; $R_2$ is hydrogen, halogen, or nitro; $R_3$ and $R_4$ are each hydrogen or halogen; and $R_5$ is alkyl of from 2 to 5 carbon atoms or cycloalkyl of 5 to 6 carbon atoms. By halogen is meant chlorine, fluorine, bromine, or iodine.

The preferred novel compounds of this invention are:
3-oxo-2-(2,4-dichlorophenyl)-4,5,6,7-tetrahydro-v-triazole (1,5-a) pyridine;
3-oxo-2-(2,4-dibromophenyl)-4,5,6,7-tetrahydro-v-triazolo (1,5-a) pyridine;
3-oxo-2-(2,4,5-trichlorophenyl)-4,5,6,7-tetrahydro-v-triazolo(1,5-a)pyridine;
3-oxo-2-(2,4,5-trichlorophenyl)-4,5,6,7-tetrahydro-v-triazolo(1,5-a)pyridine;
3-oxo-2-(2-chloro-4-bromophenyl)-4,5,6,7-tetrahydro-v-triazolo(1,5-a)pyridine.

The third object of the present invention is to provide a novel process for preparing 3-phenyl-4-oxo-1,2,3-triazoles comprising contacting a benzenediazonium chloride with an α-amino carboxylic acid in at least equimolar proportions and in an aqueous solution and subsequently cyclodehydrating the resulting 1-carboxymethyl-3-phenyl-triazene so produced by treatment with acetic anhydride and pyridine in an inert solvent.

The compounds thus defined and thus prepared are effective as herbicides in both pre- and post-emergence applications. They are suitable for selective killing or specific groups of unwanted plants, and also for the total destruction of all plants in an area.

DETAILED DESCRIPTION OF THE INVENTION

The compounds of this invention are prepared by a novel process. Previously, similar mesoionic triazole compounds were prepared by cyclodehydration procedures involving the condensation of benzenediazonium chloride with an amino acid ester (Potts and Husain, J. Org. Chem. 35:3451, 1970).

We have now found that greater yields of the desired compounds are obtained if this condensation is carried out using the amino acid rather than the amino acid ester.

An example of such a reaction is shown in the scheme below:

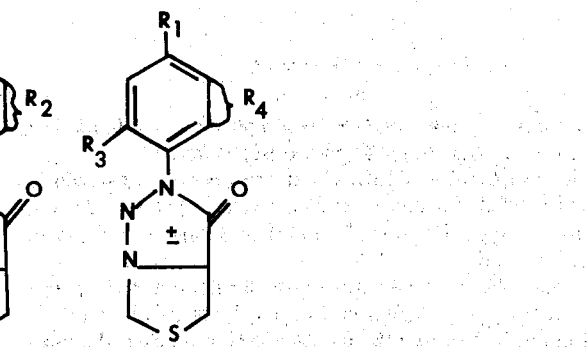

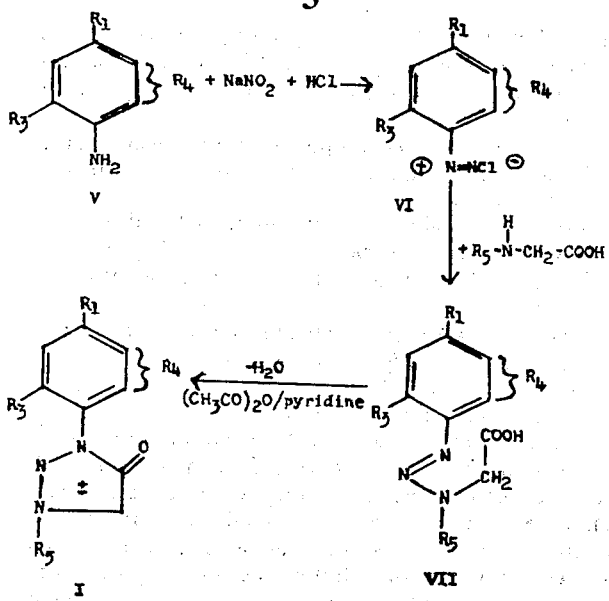

All substituents are as previously defined.

In this case a para-halogen substituted aniline (V) is reacted with nitrous acid in at least equimolar proportions to form the benzenediazoniumchloride (VI). Compound VI is then reacted with an α-amino carboxylic acid in at least equimolar proportions and in an aqueous medium to form VII. The reaction up to this point is preferably carried out in the cold, at about 0°C.

Compound VII is then dehydrated to form the desired compound I by suspending VII in ether or other inert solvents and then adding acetic anhydride followed by pyridine. This mixture is allowed to stand overnight or for a few days at room temperature. The crystalline product I may then be filtered and washed with ether, if desired.

The choice of anilines for the use in the above reaction is governed by the product desired so long as the para-halogen atom is preserved and the other substituents follow the definitions previously set forth.

The choice of amino acids useful in the above reaction is also very broad. If compounds of type I are desired, the amino acid used will be of the formula

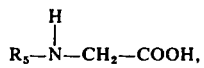

wherein $R_5$ is alkyl of 2–5 carbon atoms or cycloalkyl of 5 to 6 carbon atoms as previously stated.

If compounds of formula II are desired, pipecolinic acid is used, for compounds of type III proline is used, and for type IV compounds 4-thiazolidinecarboxylic acid is used.

This novel process is generally applicable to the preparation of any 3-phenyl-4-oxo-1,2,3-triazoline and is effected by treating the corresponding benzenediazoniumchloride with the appropriate α-amino carboxylic acid in at least equimolar proportions and in an aqueous solution, and cyclodehydrating the resulting 1-carboxymethyl-3-phenyl-triazene by treatment with acetic anhydride and pyridine in an inert solvent, preferably ether.

The 4-halophenyl herbicides of the present invention may include a variety of substituents on the halophenyl ring. This includes 4-chloro, -bromo, -fluoro or -iodophenyl groups having, for example, nitro, methyl, halogen, methoxy, trifluoromethyl, cyano, methylthio, and the like in the 2-, 5-and/or 6-positions. Ordinarily we prefer phenyl having no more than 3 substituents in the interest of ease of preparation and cost. Preferred 4-halophenyl substituents are those defined above in formulae I, II, III and IV.

The compounds of this invention may be used as suspensions, solutions, or dusts. The form of application depends upon the purpose for which the product is designed, but, in any case it should ensure a fine distribution of the active ingredient.

For the preparation of solutions to be sprayed directly on the plants, mineral oils such as diesel oil or kerosene, coal-tar oils, and other oils of animal or plant origin are suitable.

Aqueous formulations are preferred and may be prepared from emulsion concentrates, pastes, or wettable powders by adding water.

Dusts may be prepared by mixing or grinding the active compound with a suitable solid carrier.

The compounds of this invention may also be combined with known herbicidal agents if desired.

In the greenhouse and field testing of the compounds of this invention which is reported in the examples to follow, the compounds were prepared as aqueous suspensions and then applied both to soil in which seeds of crop plants and weeds had been planted and also to young plants. Results are given numerical values of from "0" for no effect to "10" for all plants killed. The dosages used varying from 0.5 to 10 lbs. per acre are reported in the following examples for each compound tested.

The compounds of this invention are preferably to be used in such a way that a dose of from about 1–10 lbs. per acre of the active ingredient will be applied. Larger or smaller doses may of course be employed, but no especial benefit will be gained by such use.

The following examples are illustrative and in no way limit the scope of the appended claims.

EXAMPLE I

In a 12 l., 3 necked round bottom flask are added 162 g. (1 mole) of 2,4-dichloroaniline, 500 ml. concentrated HCl, and 2000 ml. H₂O. The aniline was dissolved by the aid of heating on a steam bath. The solution was cooled to about 0°C., and 76 g. (1.1 mole) of sodium nitrite dissolved in 200 ml. of H₂O, were added to it. The solution was stirred for ½ hour and then a saturated solution of urea was added until a negative test with starch paper was obtained. This solution was then slowly added (over a period of about 2 hours) to a cooled solution of pipecolinic acid (129 g. - 1.0 mole) and triethylamine (416 ml. - 3 mole) in 15 l. of water. The resulting mixture was stirred for ½ hour, after which the precipitated solid was filtered and washed with water. The case was taken up in methylene chloride (1.5 l.) and the filtrate was extracted twice the methylene chloride (1 l.). The combined methylene chloride solutions were dried over anhydrous sodium sulfate and then evaporated in vacuo to afford 159 g. of an oil.

The oil was dissolved in 2 l. of ether. To this was added 200 ml. of acetic anhydride followed by 100 ml. of pyridine. The reaction mixture was allowed to stand at room temperature for 24 hours. The crystalline product was then filtered and washed with ether to yield 85 g. of a product with a melting point of 138°–139°C. The mother liquor was evaporated in vacuo to dryness. Upon addition of ether, 21 g. of the above product were obtained. A third crop of 15.5 g. of this product was also obtained upon concentration of the mother liquor. A total of 121.5 g. of anhydro-3-oxo-2-(2,4-dichlorophenyl)-4,5,6,7-tetrahydropyrido-[1,2-C]-v-triazolinium hydroxide with a melting point of 138°–139°C. was produced.

The above compound in an aqueous suspension was tested in the field in a standard pre-emergence test against Jimson weed at 10 lb./acre as previously de-

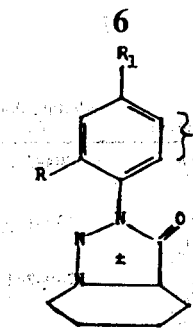

| Example No. | Substitution | Melting Point °C. | Pounds/Acre | Effect on Jimson Weed[1] Pre[2] | Post[3] |
|---|---|---|---|---|---|
| 2 | R = F, $R_1$ = F, $R_2$ = H | 125–126 | 5 | 9 | 10 |
| 3 | R = Cl, $R_1$ = Cl, $R_2$ = 5-Cl | 183–184 | 2 | 10 | 10 |
| 4 | R = Cl, $R_1$ = Cl, $R_2$ = 6-Cl | 240–242 | 2 | 9 | 10 |
| 5 | R = $NO_2$, $R_1$ = Cl, $R_2$ = H | 210–211 | 5 | 3 | 9 |

[1] Standard greenhouse herbicide tests were performed. Values of from 0 (no injury) to 10 (all plants killed).
[2] Soil treated before emergence of seedling.
[3] Plants treated after emergence from soil.

| Example No. | Substitution | Melting Point °C. | Pounds/Acre | Effect on Jimson Weed Pre | Post |
|---|---|---|---|---|---|
| 6 | R = Br, $R_1$ = Br, $R_2$ = H | 95–97 | 5 | 9 | 10 |
| 7 | R = H, $R_1$ = Cl, $R_2$ = H | 174–176 | 10 | 10 | 9 |
| 8 | R = $CH_3$, $R_1$ = Cl, $R_2$ = H | 151–152 | 5 | 9 | 7 |
| 9 | R = Cl, $R_1$ = Br, $R_2$ = H | 166–168 | 2 | 9 | 3 |
| 10 | R = $CH_3$, $R_1$ = Br, $R_2$ = H | 155–157 | 10 | 10 | 10 |
| 11 | R = Cl, $R_1$ = Cl, $R_2$ = 6-$NO_2$ | 213–214 | 10 | 10 | 10 |
| 12 | R = $CH_3$, $R_1$ = I, $R_2$ = H | 166–167 | 10 | 10 | 7 |
| 13 | R = $CH_3$, $R_1$ = F, $R_2$ = H | 171–172 | 5 | 3 | 10 | scribed, and was found to have a rating of "9"[1] in this test.

EXAMPLES II–LXIV

In the Examples to follow, the compounds were prepared and tested as in Example I using the appropriately substituted aniline and the appropriate α-amino carboxylic acid.

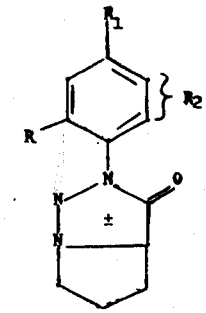

| Example No. | Substitution | Melting Point °C. | Pounds/Acre | Effect on Jimson Weed Pre | Post |
|---|---|---|---|---|---|
| 14 | R = Br, $R_1$ = Br, $R_2$ = H | 172–176 | 10 | 10 | |
| 15 | R = F, $R_1$ = F, $R_2$ = H | 125 | 5 | 8 | |

| Example No. | Substitution | Melting Point °C. | Pounds/Acre | Effect on Jimson Weed Pre | Post |
|---|---|---|---|---|---|
| 16 | R = NO$_2$<br>R$_1$ = Cl<br>R$_2$ = H | 204–205 | 5 | 3 | 9 |
| 17 | R = Cl<br>R$_1$ = Cl<br>R$_2$ = 5-Cl | 135–136 | 5 | 7 | |
| 18 | R = Cl<br>R$_1$ = Cl<br>R$_2$ = 6-Cl | 240–241 | 10 | 10 | |
| 19 | R = Cl<br>R$_1$ = Br<br>R$_2$ = H | 188–190 | 10 | 10 | 10 |
| 20 | R = CH$_3$<br>R$_1$ = Cl<br>R$_2$ = H | 178–180 | 10 | 5 | 7 |
| 21 | R = CH$_3$<br>R$_1$ = Br<br>R$_2$ = H | 198–201 | 10 | 9 | 10 |
| 22 | R = Cl<br>R$_1$ = Cl<br>R$_2$ = H | 166–167 | 5 | | 10 |
| 23 | R = Cl<br>R$_1$ = Cl<br>R$_2$ = 6-NO$_2$ | 189–193 | 10 | 10 | 10 |
| 24 | R = CH$_3$<br>R$_1$ = I<br>R$_2$ = H | 200–201 | 10 | 2 | 10 |
| 25 | R = CH$_3$<br>R$_1$ = Br<br>R$_2$ = 6-CH$_3$ | 199–201 | 5 | 5 | 10 |

30

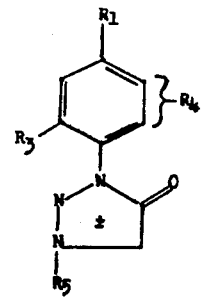

| Example No. | Substitution | Melting Point °C. | Pounds/Acre | Effect On Jimson Weed Pre | Post |
|---|---|---|---|---|---|
| 26 | R$_1$ = Cl<br>R$_3$ = Cl<br>R$_4$ = H<br>R$_5$ = n-propyl | 113–116 | 5 | 9 | 10 |
| 27 | R$_1$ = Cl<br>R$_3$ = Cl<br>R$_4$ = H<br>R$_5$ = CH$_2$CH$_3$ | 113–114 | 5 | 10 | |
| 28 | R$_1$ = Br<br>R$_3$ = Br<br>R$_4$ = H<br>R$_5$ = CH$_2$CH$_3$ | 120–125 | | | |
| 29 | R$_1$ = Br<br>R$_3$ = Cl<br>R$_4$ = H<br>R$_5$ = t-butyl | 195–197 | 5 | 10 | 10 |
| 30 | R$_1$ = Cl<br>R$_3$ = Cl<br>R$_4$ = 5-Cl<br>R$_5$ = i-propyl | 151–154 | 5 | 9 | 10 |
| 31 | R$_1$ = Cl<br>R$_3$ = Cl<br>R$_4$ = 5-Cl<br>R$_5$ = t-butyl | 171–172 | 5 | 10 | 10 |
| 32 | R$_1$ = Cl<br>R$_3$ = Cl<br>R$_4$ = 6-Cl<br>R$_5$ = i-propyl | 210–211 | 5 | 10 | 8 |
| 33 | R$_1$ = Br<br>R$_3$ = CH$_3$<br>R$_4$ = H<br>R$_5$ = i-propyl | 138–139 | 5 | 5 | 10 |
| 34 | R$_1$ = Cl<br>R$_3$ = NO$_2$<br>R$_4$ = H<br>R$_5$ = i-propyl | 174–175 | 5 | 0 | 10 |
| 35 | R$_1$ = Cl<br>R$_3$ = NO$_2$<br>R$_4$ = H<br>R$_5$ = t-butyl | 155–156 | 5 | 2 | 10 |
| 36 | R$_1$ = Cl | 148–150 | 5 | 8 | 10 |

-continued

| Example No. | Substitution | Melting Point °C. | Pounds/Acre | Effect On Jimson Weed Pre | Post |
|---|---|---|---|---|---|
| 37 | $R_5$ = s-butyl $R_1$ = Br $R_3$ = Cl $R_4$ = H | 149–151 | 5 | 8 | 9 |
| 38 | $R_5$ = s-butyl $R_1$ = Cl $R_3$ = Cl $R_4$ = H | 194–196 | 5 | 6 | 10 |
| 39 | $R_5$ = i-butyl $R_1$ = Br $R_3$ = Cl $R_4$ = H | 190–192 | 5 | 5 | 10 |
| 40 | $R_5$ = i-butyl $R_1$ = Br $R_3$ = Cl $R_4$ = H | 113–115 | 5 | 0 | 10 |
| 41 | $R_5$ = n-pentyl $R_1$ = Br $R_3$ = Cl $R_4$ = H | 172–174 | 5 | 0 | 8 |
| 42 | $R_5$ = i-butyl $R_1$ = Br $R_3$ = Cl $R_4$ = H | 163–165 | 5 | 2 | 9 |
| 43 | $R_5$ = i-pentyl $R_1$ = Cl $R_3$ = Cl $R_4$ = H | 205–206 | 5 | 4 | 10 |
| 44 | $R_5$ = cyclohexyl $R_1$ = Cl $R_3$ = Cl $R_4$ = 5-Cl | 160–162 | 5 | 4 | 10 |
| 45 | $R_5$ = s-butyl $R_1$ = Cl $R_3$ = Cl $R_4$ = 5-Cl | 151–152 | 5 | 2 | 10 |
| 46 | $R_5$ = i-butyl $R_1$ = Br $R_3$ = Cl $R_4$ = H | 142–143 | 5 | 5 | 9 |
| 47 | $R_5$ = i-pentyl $R_1$ = Br $R_3$ = Cl $R_4$ = H | 296–297 | 5 | 6 | 10 |
| 48 | $R_5$ = cyclohexyl $R_1$ = Cl $R_3$ = Cl $R_4$ = H | 142–144 | 5 | 5 | 10 |
| 49 | $R_5$ = i-pentyl $R_1$ = Cl $R_3$ = Cl $R_4$ = H | 185–186 | 5 | 8 | 10 |
| 50 | $R_5$ = cyclopentyl $R_1$ = Cl $R_3$ = $CH_3$ $R_4$ = H | 163–165 | 5 | 5 | 10 |
| 51 | $R_5$ = cyclopentyl $R_1$ = Cl $R_3$ = Cl $R_4$ = H | 113–116 | 5 | 9 | 10 |
| 52 | $R_5$ = n-propyl $R_1$ = Br $R_3$ = Cl $R_4$ = H | 120–125 | 10 | 9 | |
| 53 | $R_5$ = $CH_2CH_3$ $R_1$ = Cl $R_3$ = Cl $R_4$ = 5-Cl | 126–128 | 10 | 10 | |
| 54 | $R_5$ = $CH_2CH_3$ $R_1$ = Cl $R_3$ = Cl $R_4$ = H | 173–174 | 10 | 9 | 9 |
| 55 | $R_5$ = n-butyl $R_1$ = Cl $R_3$ = Cl $R_4$ = 5-Cl | 93–94 | 5 | 1 | 7 |
| 56 | $R_5$ = n-butyl $R_1$ = Cl $R_3$ = Cl $R_4$ = 6-Cl | 144–147 | 5 | 5 | 5 |
| 57 | $R_5$ = n-butyl $R_1$ = Br $R_3$ = Cl $R_4$ = H | 175–177 | 5 | 3 | 8 |
| 58 | $R_5$ = n-butyl $R_1$ = Cl $R_3$ = Cl $R_4$ = H | 156–158 | 2 | 8 | 10 |

| Example No. | Substitution | Melting Point °C. | Pounds/Acre | Effect On Jimson Weed Pre | Post |
|---|---|---|---|---|---|
| 59 | $R_5$ = i-propyl<br>$R_1$ = Br<br>$R_3$ = Cl<br>$R_4$ = H | 160–162 | 5 | 9 | 10 |
| 60 | $R_5$ = i-propyl<br>$R_1$ = Cl<br>$R_3$ = Cl<br>$R_4$ = H<br>$R_5$ = t-butyl | 180–182 | 0.5 | 1 | 10 |

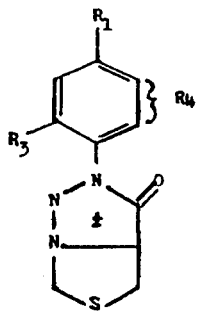

| Example No. | Substitution | Melting Point °C. | Pounds/Acre | Effect on Jimson Weed Pre | Post |
|---|---|---|---|---|---|
| 61 | $R_1$ = Cl<br>$R_3$ = Cl<br>$R_4$ = H | 160.5–162 | 10 | 10 | 10 |
| 62 | $R_1$ = Cl<br>$R_3$ = Cl<br>$R_4$ = 6-Cl | 203–204 | 10 | 10 | 10 |
| 63 | $R_1$ = F<br>$R_3$ = F<br>$R_4$ = H | 168–170 | 10 | 10 | 10 |
| 64 | $R_1$ = Cl<br>$R_3$ = Cl<br>$R_4$ = 5-Cl | 182–184 | 10 | 10 | 10 |

EXAMPLES 65–69

Standard herbicide field tests were performed as before using some of the foregoing compounds but with different plants. In the examples to follow the "compound number" refers to earlier example numbers. The following abbreviations are used: SOYB = soybean, MNGY = wild morningglory, PIGW = pigweed, BNGS = barnyardgrass, and YNSG = yellow nutsedge. The pre- and post-emergence tests were performed as previously described and the rating system is the same as that used in the greenhouse tests.

What is claimed is:
1. A compound of the formula

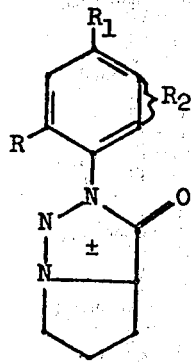

wherein
R is hydrogen, halogen, methyl, or nitro;
$R_1$ is halogen; and
$R_2$ is hydrogen, halogen, or nitro.
2. 3-oxo-2-(2,4-dichlorophenyl)-5,6-dihydro-4(H)-pyrrolo-[1,2-C]-v-triazole.

* * * * *

| Example No. | Compound No. | lbs/acre | SOYB Pre | SOYB Post | CORN Pre | CORN Post | MNGY Pre | MNGY Post | PIGW Pre | PIGW Post | BNGS Pre | BNGS Post | YNSG Pre | YNSG Post |
|---|---|---|---|---|---|---|---|---|---|---|---|---|---|---|
| 65 | 22 | 8 | 2 | 6 | 2 | 2 | 3 | 7 | 0 | 10 | 5 | 4 | 0 | 1 |
| 66 | 1 | 8 | 4 | 9 | 3 | 4 | 6 | 9 | 9 | 10 | 10 | 8 | 5 | 3 |
| 67 | 3 | 8 | 2 | ND | 2 | ND | 3 | ND | 10 | ND | 3 | ND | 3 | ND |
| 68 | 2 | 5 | 0 | 0 | 0 | 0 | 0 | 10 | 0 | 9 | 0 | 0 | 0 | 0 |
| 69 | 4 | 10 | ND | ND | 5 | 0 | 10 | 10 | 10 | 9 | 9 | 8 | 5 | 3 |

*not done